United States Patent [19]
Horwitz et al.

[11] Patent Number: 6,087,126
[45] Date of Patent: Jul. 11, 2000

[54] BACTERICIDAL/PERMEABILITY-INCREASING PROTEIN (BPI) DELETION ANALOGS

[75] Inventors: Arnold Horwitz, Los Angeles; Stephen F. Carroll, Walnut Creek; David Burke, Oakland, all of Calif.

[73] Assignee: XOMA Corporation, Berkeley, Calif.

[21] Appl. No.: 09/336,402

[22] Filed: Jun. 18, 1999

Related U.S. Application Data

[63] Continuation-in-part of application No. 09/099,725, Jun. 19, 1998, Pat. No. 6,013,631.

[51] Int. Cl.[7] .......................... C12P 21/06; C12N 15/00; C12N 5/00; C12N 5/06; C07H 21/04
[52] U.S. Cl. .................. 435/69.1; 435/320.1; 435/325; 435/358; 536/23.2
[58] Field of Search .................. 536/23.2; 435/320.1, 435/69.1, 325, 358; 514/12

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott et al. | 514/12 |
| 5,198,541 | 3/1993 | Elsbach et al. | 435/69.1 |
| 5,234,912 | 8/1993 | Marra et al. | 514/12 |
| 5,308,834 | 5/1994 | Scott et al. | 514/12 |
| 5,334,584 | 8/1994 | Scott et al. | 514/12 |
| 5,348,942 | 9/1994 | Little II et al. | 514/12 |
| 5,420,019 | 5/1995 | Theofan et al. | 435/69.1 |
| 5,439,807 | 8/1995 | Grinna et al. | 435/69.1 |
| 5,447,913 | 9/1995 | Ammons et al. | 514/12 |
| 5,466,580 | 11/1995 | White et al. | 435/7.1 |
| 5,466,581 | 11/1995 | White et al. | 435/7.32 |
| 5,484,705 | 1/1996 | White et al. | 435/7.32 |

(List continued on next page.)

FOREIGN PATENT DOCUMENTS

| | | |
|---|---|---|
| WO 90/09183 | 8/1990 | WIPO . |
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |
| WO 94/21280 | 9/1994 | WIPO . |
| WO 94/25476 | 11/1994 | WIPO . |
| WO 95/00641 | 1/1995 | WIPO . |
| WO 95/01428 | 1/1995 | WIPO . |
| WO 95/02414 | 1/1995 | WIPO . |
| WO 95/08344 | 3/1995 | WIPO . |
| WO 95/08773 | 3/1995 | WIPO . |
| WO 95/10297 | 4/1995 | WIPO . |
| WO 95/19179 | 7/1995 | WIPO . |

(List continued on next page.)

OTHER PUBLICATIONS

Ammons et al., "Protective Effects of an N–Terminal Fragment of Bactericidal/Permeability–Increasing Protein in Endotoxemia and Gram–Negative Sepsis," in *Novel Therapeutics Strategies in the Treatment of Sepsis*, Morrison and Ryan, eds., Marcel Dekker, New York, pp. 55–70 (1996).

(List continued on next page.)

*Primary Examiner*—Karen Cochrane Carlson
*Assistant Examiner*—Devesh Srivastava
*Attorney, Agent, or Firm*—Marshall, O'Toole, Gerstein, Murray & Borun

[57] ABSTRACT

Novel BPI deletion analogs are provided that consist of amino acid residues 10 through 193 of mature human BPI wherein the cysteine residue at BPI amino acid position 132 is replaced by another amino acid. Fusion proteins comprising these analogs are also provided, as are polynucleotides encoding these products, materials and methods for their recombinant production, compositions and medicaments of these products, and therapeutic uses for these products.

10 Claims, 1 Drawing Sheet

U.S. PATENT DOCUMENTS

| | | | |
|---|---|---|---|
| 5,488,034 | 1/1996 | McGregor et al. | 514/12 |
| 5,494,896 | 2/1996 | Hansbrough | 514/12 |
| 5,523,288 | 6/1996 | Cohen et al. | 514/12 |
| 5,532,216 | 7/1996 | Espevik et al. | 514/12 |
| 5,576,292 | 11/1996 | Elsbach et al. | 514/12 |
| 5,578,568 | 11/1996 | Ammons et al. | 514/12 |
| 5,578,572 | 11/1996 | Horwitz et al. | 514/12 |
| 5,627,153 | 5/1997 | Little et al. | 514/12 |
| 5,639,727 | 6/1997 | Little et al. | 514/12 |
| 5,641,874 | 6/1997 | Elsbach et al. | 536/23.1 |
| 5,643,570 | 7/1997 | Theofan et al. | 424/134.1 |
| 5,643,875 | 7/1997 | Friedman et al. | 514/12 |
| 5,646,114 | 7/1997 | Lambert | 514/12 |
| 5,652,332 | 7/1997 | Little | 530/324 |
| 5,674,834 | 10/1997 | Theofan et al. | 514/12 |
| 5,686,414 | 11/1997 | Scannon | 514/12 |
| 5,696,090 | 12/1997 | McGregor et al. | 514/12 |
| 5,703,038 | 12/1997 | Ammons et al. | 514/2 |
| 5,731,415 | 3/1998 | Gazzano-Santoro et al. | 530/350 |
| 5,733,872 | 3/1998 | Little | 514/12 |
| 5,741,779 | 4/1998 | White et al. | 514/12 |
| 5,753,620 | 5/1998 | Friedmann et al. | 514/12 |
| 5,756,464 | 5/1998 | Scannon et al. | 514/12 |
| 5,763,567 | 6/1998 | Little, II | 530/300 |
| 5,770,561 | 6/1998 | Horwitz et al. | 514/8 |
| 5,770,694 | 6/1998 | Scott et al. | 530/350 |
| 5,783,561 | 7/1998 | Horwitz et al. | 514/12 |
| 5,786,324 | 7/1998 | Gray et al. | 514/9 |
| 5,804,367 | 9/1998 | White et al. | 435/4 |
| 5,807,818 | 9/1998 | Little, II | 514/2 |
| 5,821,064 | 10/1998 | White et al. | 435/7.1 |
| 5,827,816 | 10/1998 | Theofan et al. | 514/2 |
| 5,837,678 | 11/1998 | Little, II | 514/12 |

FOREIGN PATENT DOCUMENTS

| | | |
|---|---|---|
| WO 95/19180 | 7/1995 | WIPO . |
| WO 95/19372 | 7/1995 | WIPO . |
| WO 95/19784 | 7/1995 | WIPO . |
| WO 95/20163 | 7/1995 | WIPO . |
| WO 95/24209 | 9/1995 | WIPO . |
| WO 96/01647 | 1/1996 | WIPO . |
| WO 96/08509 | 3/1996 | WIPO . |
| WO 96/21436 | 7/1996 | WIPO . |
| WO 96/30037 | 10/1996 | WIPO . |
| WO 97/04008 | 2/1997 | WIPO . |
| WO 97/17989 | 5/1997 | WIPO . |
| WO 97/17990 | 5/1997 | WIPO . |
| WO 97/42966 | 11/1997 | WIPO . |
| WO 97/42967 | 11/1997 | WIPO . |
| WO 97/44056 | 11/1997 | WIPO . |
| WO 98/06415 | 2/1998 | WIPO . |
| WO 98/19694 | 5/1998 | WIPO . |

OTHER PUBLICATIONS

Beamer, L.J. et al., "Crystal Structure of Human BPI and Two Bound Phospholipids at 2.4 Angstrom Resolution," *Science*, 276:1861–1864 (Jun. 20, 1997).

Capodici, C. et al, "Both N– and C–Terminal Regions of the Bioactive N–Terminal Fragment of the Neutrophil Granule Bactericidal/Permeability–Increasing Protein Are Required for Stability and Function," *J. Immunology*, 156:4789–4796 (1996).

Dedrick, R.L. et al., "Elevated levels of lipopolysaccharide (LPS) binding protein (LBP) reduce the inflammatory potential of LPS in vitro and in vivo," CG 0356: Russ Dedrick; IES; Oct 20–22, 1996; Nagoya, Japan.

Elbach, P. et al., "Oxygen–Independent Antimicrobial Systems of Phagocytes", in *Inflammation: Basic Principles and Clinical Correlates*, Second Edition, eds. Gallin et al., Chapter 30, Raven Press, Ltd., New York (1992).

Elsbach, P. et al., "Separation and Purification of a Potent Bactericidal/Permeability–increasing Protein and a Closely Associated Phospholipase $A_2$ from Rabbit Polymorphonuclear Leukocytes," *J. Biological Chemistry*, 254:11000–11009 (1979).

Gazzano–Santoro et al., "High–Affinity Binding of the Bactericidal/Permeability–Increasing Protein and a Recombinant Amino–Terminal Fragment to the Lipid A Region of Lipopolysaccharide," *Infection and Immunity*, 60:4754–4761 (1992).

Gray P.W. et al., "Cloning of the cDNA of a Human Neutrophil Bactericidal Protein", *J. Biologic Chemistry*, 264(16):9505–9509 (Jun. 5, 1989).

Horwitz et al., "Expression and Characterization of Cysteine–Modified Variants of an Amino–Terminal Fragment of Bactericidal/Permeability–Increasing Protein," *Protein Expression Purification*, 8:28–40 (1996).

Horwitz, A.H. et al., "Human Lipopolysaccharide–Binding Protein Potentiates Bactericidal Activity of Human Bactericidal/Permeability–Increasing Protein," *Infection and Immunity*, 63(2):522–527 (Feb. 1995).

In't Veld et al., "Effects of the Bactericidal/Permeability-–Increasing Protein of Polymorphonuclear Leukocytes on Isolated Bacterial Cytoplasmic Membrane Vesicles", *Infection and Immunity*, 56(5):1203–1208 (May, 1988).

Mannion, B.A. et al., "Separation of Sublethal and Lethal Effects of the Bactericidal/Permeability Increasing Protein on *Escherochia coli*," *J. Clinical Investigation*, 85:853–860 (1990).

Mannion, B.A. et al., "Separation of Sublethal and Lethal Effects of Polymorphonuclear Leukocytes on *Escherichia coli*," *J. Clinical Investigation*, 86:631–641 (1990).

Ooi, C.E. et al., "Endotoxin Neutralizing Properties of the 25 kD N–Terminal Fragment of the 55–60 kD Bactericidal/ Permeability–increasing Protein of Human Neutrophils," *J. Exp. Med.*, 174:649–655 (Sep., 1991).

Ooi, C.E. et al., "A 25–kDa $NH_2$ –terminal Fragment Carries All the Antibacterial Activities of the Human Neutrophil 60–kDa Bactericidal/Permeability–increasing Protein," *J. Biological Chemistry*, 262:14891–14894 (1987).

Weiss, J. et al., "Resistance of Gram–negative Bacteria to Purified Bactericidal Leukocyte Proteins," *J. Clinical Investigation*, 65:619–628 (1980).

Weiss et al., "The Role of Lipopolysaccharide in the Action of the Bactericidal/Permeability Neutrophil Protein on the Bacterial Envelope", *J. Immunol.*, 132:3109–3115 (Jun., 1984).

Weiss et al., "Cellular and Subcellular Localization of the Bactericidal/Permeability–Increasing Protein of Neutrophils," *Blood*, 69(2):652–659 (1987).

6,087,126

BACTERICIDAL/PERMEABILITY-INCREASING PROTEIN (BPI) DELETION ANALOGS

This application is a continuation-in-part of U.S. Ser. No. 09/099,725 filed Jun. 19, 1998 now U.S. Pat. No. 6,013,631.

BACKGROUND OF THE INVENTION

The present invention provides preparations of novel biologically active deletion analogs of bactericidal/permeability-increasing protein (BPI) characterized by improved stability and homogeneity as well as by enhanced in vivo activity, and pharmaceutical compositions containing the same.

BPI is a protein isolated from the granules of mammalian polymorphonuclear leukocytes (PMNs or neutrophils), which are blood cells essential in the defense against invading microorganisms. BPI is known to bind to lipopolysaccharide, a major component of the outer membrane of gram-negative bacteria that stimulates a potent inflammatory response which can lead to septic shock. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 1 hereto. U.S. Pat. No. 5,198,541, the disclosure of which is incorporated herein by reference, discloses recombinant genes encoding, and methods for expression of, BPI proteins including recombinant BPI holoprotein, referred to as rBPI, and recombinant fragments of BPI.

A proteolytic N-terminal fragment of BPI having a molecular weight of about 25 kD has an amphipathic character, containing alternating hydrophobic and hydrophilic regions. This N-terminal fragment of human BPI possesses the anti-bacterial activity of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. [Gazzano-Santoro et al., *Infect. Immun.* 60:4754–4761 (1992).] An N-teminal analog of BPI, rBPI$_{21}$, has been produced as described in Horwitz et al., *Protein Expression Purification,* 8:28–40 (1996).

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). This reported target cell specificity was believed to be the result of the strong attraction of BPI for lipopolysaccharide (LPS), which is unique to the outer membrane (or envelope) of gram-negative organisms. Although BPI was commonly thought to be non-toxic for other microorganisms, including yeast, and for higher eukaryotic cells, it has recently been discovered, as discussed infra, that BPI protein products, exhibit activity against gram-positive bacteria, mycoplasma, mycobacteria, fungi, protozoa, and chlamydia.

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups of LPS, which normally stabilize the outer membrane through binding of $Mg^{++}$ and $Ca^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [Weiss et al., *J. Clin. Invest.* 65: 619–628 (1980)]. This first stage of BPI action, permeabilization of the gram-negative outer envelope, is reversible upon dissociation of the BPI, a process requiring high concentrations of divalent cations and synthesis of new LPS [Weiss et al., *J. Immunol.* 132: 3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et al., *J. Clin. Invest.* 86: 631–641 (1990)). Specific investigation of this possibility has shown that on a molar basis BPI is at least as inhibitory of cytoplasmic membrane vesicle function as polymyxin B (In't Veld et al., *Infection and Immunity* 56: 1203–1208 (1988)) but the exact mechanism as well as the relevance of such vesicles to studies of intact organisms has not yet been elucidated.

BPI protein products (which include naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides) have been demonstrated to have a variety of beneficial activities. BPI protein products are known to be bactericidal for gram-negative bacteria, as described in U.S. Pat. Nos. 5,198,541 and 5,523,288, both of which are incorporated herein by reference. BPI protein products are also known to enhance the effectiveness of antibiotic therapy in gram-negative bacterial infections, as described in U.S. Pat. No. 5,523,288 and corresponding International Publication No. WO 95/08344 (PCT/US94/11225), which are incorporated herein by reference. BPI protein products are also known to be bactericidal for gram-positive bacteria and mycoplasma, and to enhance the effectiveness of antibiotics in gram-positive bacterial infections, as described in U.S. Pat. No. 5,578,572 and corresponding International Publication No. WO 95/19180 (PCT/US95/00656), which are incorporated herein by reference. BPI protein products are further known to exhibit anti-fungal activity, and to enhance the activity of other anti-fungal agents, as described in U.S. Pat. No. 5,627,153 and corresponding International Publication No. WO 95/19179 (PCT/US95/00498), and further as described for anti-fungal peptides in co-owned, co-pending U.S. application Ser. No. 08/621,259 filed Mar. 21, 1996, which is in turn a continuation-in-part of U.S. application Ser. No. 08/504,841 filed Jul. 20, 1994 and corresponding International Publication Nos. WO 96/08509 (PCT/US95/09262) and WO 97/04008 (PCT/US96/03845), all of which are incorporated herein by reference. BPI protein products are further known to exhibit anti-protozoan activity, as described in U.S. Pat. No. 5,646,114 and corresponding International Publication No. WO 96/01647 (PCT/US95/08624), all of which are incorporated herein by reference. BPI protein products are known to exhibit anti-chlamydial activity, as described in co-owned, co-pending U.S. application Ser. No. 08/694,843 filed Aug. 9, 1996 and corresponding International Publication No. WO 98/06415 (PCT/US97/13810), all of which are incorporated herein by reference. Finally, BPI protein products are known to exhibit anti-mycobacterial activity, as described in co-owned, co-pending U.S. application Ser. No. 08/626,646 filed Apr. 1, 1996, which is in turn a continuation of U.S. application Ser. No. 08/285,803 filed Aug. 14, 1994, which is in turn a continuation-in-part of U.S. application Ser. No. 08/031,145 filed Mar. 12, 1993 and corresponding International Publication No. W094/20129 (PCT/US94/02463), all of which are incorporated herein by reference.

The effects of BPI protein products in humans with endotoxin in circulation, including effects on TNF, IL-6 and endotoxin are described in U.S. Pat. Nos. 5,643,875 and 5,753,620 and corresponding International Publication No. WO 95/19784 (PCT/US95/01151), all of which are incorporated herein by reference.

BPI protein products are also known to be useful for treatment of specific disease conditions, such as meningococcemia in humans (as described in co-owned, co-pending U.S. application Ser. No. 08/644,287 filed May 10, 1996 and corresponding International Publication No. WO 97/42966 (PCT/US97/08016), which are incorporated herein by reference), hemorrhagic trauma in humans, (as described in co-owned, co-pending U.S. application Ser. No. 08/862,785, a continuation-in-part of U.S. Ser. No. 08/652,292 filed May 23, 1996, now U.S. Pat. No. 5,756,464, and corresponding International Publication No. WO 97/44056 (PCT/US97/08941), all of which are incorporated herein by reference), burn injury (as described in U.S. Pat. No. 5,494,896 and corresponding International Publication No. WO 96/30037 (PCT/US96/02349), both of which are incorporated herein by reference), ischemia/reperfusion injury (as described in U.S. Pat. No. 5,578,568, incorporated herein by reference), and liver resection (as described in co-owned, co-pending U.S. application Ser. No. 08/582,230 filed Mar. 16, 1998 which is a continued prosecution application of the same serial no. filed Jan. 3, 1996, which is in turn a continuation of U.S. application Ser. No. 08/318,357 filed Oct. 5, 1994, which is in turn a continuation-in-part of U.S. application Ser. No. 08/132,510 filed Oct. 5, 1993, and corresponding International Publication No. WO 95/10297 (PCT/US94/11404), all of which are incorporated herein by reference).

BPI protein products are also known to neutralize the anti-coagulant activity of exogenous heparin, as described in U.S. Pat. No. 5,348,942, incorporated herein by reference, as well as to be useful for treating chronic inflammatory diseases such as rheumatoid and reactive arthritis, as described in U.S. Pat. No. 5,639,727, incorporated herein by reference, and for inhibiting angiogenesis and for treating angiogenesis-associated disorders including malignant tumors, ocular retinopathy and endometriosis, as described in co-owned, co-pending U.S. application Ser. Nos. 08/435,855, 08/466,624 and 08/466,826, and corresponding International Publication No. WO 94/20128 (PCT/US94/02401), all of which are incorporated herein by reference.

BPI protein products are also known for use in antithrombotic methods, as described in U.S. Pat. No. 5,741,779 and corresponding International Publication No. W097/42967 (PCT/US97/08017), which are incorporated herein by reference.

U.S. Pat. Nos. 5,420,019 and 5,674,834 and corresponding International Publication No. W094/18323 (PCT/US94/01235), all of which are incorporated herein by reference, discloses that the replacement of the cysteine residue at amino acid position 132 or 135 with another amino acid renders the resulting BPI polypeptide resistant to dimerization and cysteine adduct formation. It also discloses that terminating the N-terminal BPI fragment at BPI amino acid position 193 resulted in an expression product with reduced carboxy-terminal heterogeneity.

Of interest is the report in Capodici and Weiss, *J. Immunol.*, 156:4789–4796 (1996) that the in vitro transcription/translation products of DNA encoding amino acid residues 1 through 193 ($BPI_{1-193}$) and residues 13 through 193 ($BPI_{13-193}$) of mature BPI showed similar LPS-dependent binding to immobilized LPS.

There continues to be a need in the art for improved biologically active BPI protein product preparations, particularly those with enhanced stability, homogeneity and/or in vivo biological activity.

SUMMARY OF THE INVENTION

The present invention provides novel biologically active BPI deletion analogs and preparations thereof characterized by enhanced stability and homogeneity, including for example, resistance to dimerization and cysteine adduct formation and reduced amino-terminal and carboxy-terminal heterogeneity of the recombinant product, as well as by enhanced in vivo biological activity, properties which render it highly suitable for therapeutic and diagnostic uses. Novel BPI deletion analogs are the expression product of DNA encoding amino acid residues 10 through 193 of mature human BPI (SEQ ID NO: 2), in which the cysteine at position 132 has been replaced with a different amino acid, preferably a non-polar amino acid such as serine or alanine. In a preferred embodiment, designated "rBPI (10–193)C132A" or "rBPI(10–193)ala$^{132}$," the cysteine at position 132 is replaced with an alanine.

The invention further provides novel purified and isolated polynucleotide sequences (e.g., DNA or RNA) encoding these BPI protein products; materials and methods for their recombinant production, including vectors and host cells comprising the DNA; improved stable pharmaceutical compositions comprising these BPI protein products; and improved treatment methods using these compositions, either alone or concurrently administered with other therapeutic agents. Also contemplated is the use of the BPI deletion analogs of the invention in manufacture of a medicament for treating a subject that would benefit from administration of BPI protein product.

Numerous additional aspects and advantages of the invention will become apparent to those skilled in the art upon considering the following detailed description of the invention, which describes the presently preferred embodiments thereof.

DETAILED DESCRIPTION OF THE INVENTION

Figure 1:
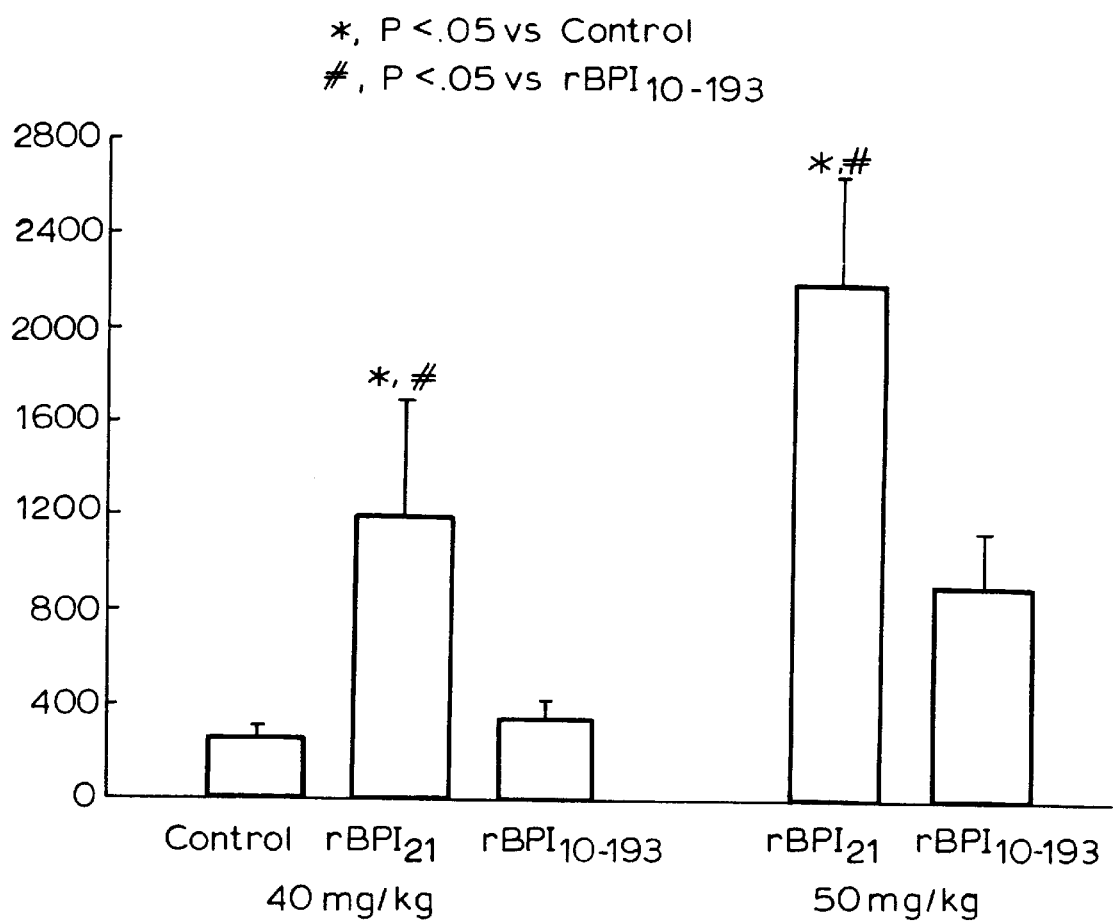
FIG. 1 depicts the elevation in blood pressure, measured as area under the curve (AUC) occurring after administration of either rBPI(10–193)C132A or rBPI$_{21}$.

The present invention provides novel BPI deletion analogs consisting of amino acid residues 10 through 193 of mature human BPI (set forth in SEQ ID NO: 2) wherein the cysteine residue at BPI amino acid position 132 is replaced by another amino acid, preferably a non-polar amino acid such as serine or alanine. A preferred embodiment, in which the cysteine at position 132 is replaced with an alanine, has been designated rBPI(10–193)C132A or rBPI(10–193)ala$^{132}$.

The BPI protein product rBPI$_{21}$ is the expression product of DNA encoding amino acid residues 1 to 193 of mature human BPI wherein the cysteine at residue number 132 is substituted with alanine, described in U.S. Pat. No. 5,420,019. Changes in the fermentation processes used to produce rBPI$_{21}$ by recombinant methods that achieved higher cell densities and higher rBPI$_{21}$ titers also resulted in an apparent increase in amino-terminal heterogeneity of the purified product. In some fermentation runs, up to about 20 % of the purified product was observed to be a species with amino acids 10–193 of BPI, rather than the encoded 1–193 amino acids. SDS-PAGE gels of 500-liter fermentor samples over the course of a fermentation run showed that this 10–193 species appeared in the last 2–3 days of the run, with the greatest amount appearing on the day of harvest. Further investigation revealed that incubation of rBPI$_{21}$ with a CHO-K1 cell homogenate yielded a digested product, suggesting that protease activity associated with the cells was involved. To simulate protease activity in a controlled manner, rBPI$_{21}$ was incubated with aminopeptidase M and elastase. The rBPI$_{21}$ was resistant to aminopeptidase M digestion, but elastase rapidly converted the rBPI$_{21}$ into 40 % BPI(8–193) and 60% BPI(10–193).

As described herein, stable homogeneous preparations of rBPI(10–193)C132A were produced proteolytically and by recombinant methods. The protein was purified and was tested for biological activity. Experiments were performed to compare rBPI(10–193)C132A to rBPI$_{21}$ in several in vitro biological assays, two different animal efficacy models and in pharmacokinetic and toxicology studies. As described in Examples 5–7, rBPI(10–193)C132A and rBPI$_{21}$ had similar in vitro activities when compared in radial diffusion and broth microdilution bactericidal assays with *Escherichia coli* J5, a radial diffusion assay with an L-form of *Staphylococcus aureus*, a competition binding assay with *E. coli* J5 LPS, and in LPS neutralization assays with RAW and THP1 cells. Additional experiments described in Example 5 showed that rBPI(10–193)C132A appeared to be approximately twice as potent as rBPI$_{21}$ in an LPS binding assay using rate nephelometry. As described in Example 8, purified rBPI(10–193)C132A and rBPI$_{21}$ had similar toxicity profiles in a GLP toxicology study in rats at doses up to 120 mg/kg/day for three days and similar pharmacokinetics in rats at a dose of 2 mg/kg. Experiments described in Example 8 also showed that in a mouse endotoxin challenge model, rBPI(10–193)C132A appeared to be at least two-fold more potent than rBPI$_{21}$ in two studies whereas in a mouse model of lethal bacteremia, rBPI(10–193)C132A and rBPI$_{21}$ were similarly potent. In additional in vivo experiments in conscious rats, doses of 40 and 50 mg/kg of infused rBPI$_{21}$ caused significant transient decreases in blood pressure relative to the vehicle control, while the same doses of rBPI(10–193)C132A did not result in a statistically significant transient decrease in blood pressure relative to control. Thus, infusion of rBPI(10–193)C132A appears to provide a reduction in an adverse effect in blood pressure compared with infusion of rBPI$_{21}$.

The invention further contemplates fusion of rBPI (10–193)C132A with at least a portion of at least one other polypeptide. Examples of such hybrid fusion proteins are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

The invention additionally contemplates purified and isolated polynucleotide sequences (e.g., DNA or RNA) encoding the novel BPI deletion analogs or fusion proteins of the present invention; expression vectors containing such polynucleotides, preferably operatively linked to an endogenous or heterologous expression control sequence; prokaryotic or eukaryotic host cells stably transfected or transformed with a DNA or vector of the present invention; and methods for the recombinant production of the novel deletion analog BPI protein products of the present invention, e.g., methods in which a host cell is grown in a suitable nutrient medium and the deletion analog BPI protein product is isolated from the cell or the medium. Such polynucleotide sequences or vectors may optionally encode the 27-amino acid BPI leader sequence and the mouse light chain polyadenylation signal.

The recombinantly produced novel BPI deletion analog of the present invention may be produced according to the methods described in U.S. Pat. No. 5,439,807 and corresponding International Publication No. WO 93/23540 (PCT/US93/04752), which are all incorporated herein by reference. U.S. Pat. No. 5,439,807 discloses methods for the purification of recombinant BPI protein products expressed in and secreted from genetically transfected mammalian host cells in culture, and discloses how one may produce large quantities of recombinant BPI products suitable for incorporation into stable, homogeneous pharmaceutical preparations.

The present invention further provides improved stable pharmaceutical compositions comprising the novel BPI deletion analogs and improved treatment methods using these compositions, either alone or concurrently administered with other therapeutic agents. It is contemplated that such compositions may be utilized in any of the therapeutic uses known for BPI protein products, including those discussed supra.

The administration of BPI protein products in general, including BPI deletion analogs, is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known antichlamydial agents. A stable pharmaceutical composition containing BPI protein products (e.g., $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF, Parsippany, N.J.) and 0.002% by weight of polysorbate 80 (Tween 80, ICI Americas Inc., Wilmington, Del. or JT Baker, Phillipsburg, N.J.). Another stable pharmaceutical composition containing BPI protein products (e.g., $rBPI_{21}$) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034 and 5,696,090 and corresponding International Publication No. WO 94/17819 (PCT/US94/01239), the disclosures of all of which are incorporated herein by reference. As described in U.S. application Ser. No. 08/586,133 filed Jan. 12, 1996, which is in turn a continuation-in-part of U.S. application Ser. No. 08/530,599 filed Sep. 19, 1995, which is in turn a continuation-in-part of U.S. application Ser. No. 08/372,104 filed Jan. 13, 1995, and corresponding International Publication No. W096/21436 (PCT/US96/01095), all of which are incorporated herein by reference, other poloxamer formulations of BPI protein products with enhanced activity may be utilized.

Therapeutic compositions comprising BPI protein product may be administered systemically or topically. Systemic routes of administration include oral and parenteral routes, including intravenous, intramuscular or subcutaneous injection (including into a depot for long-term release), intraocular and retrobulbar, intrathecal, intraperitoneal (e.g. by intraperitoneal ravage), intrapulmonary (using powdered drug, or an aerosolized or nebulized drug solution), or transdermal. Improved aerosolized formulations are described in co-owned, co-pending U.S. application Ser. No. 08/962,217 filed Oct. 31, 1997 and corresponding International Publication No. WO 98/19694 (PCT/US97/19850), which are both incorporated herein by reference.

When given parenterally, BPI protein product compositions are generally injected in doses ranging from 1 μg/kg to 100 mg/kg per day, preferably at doses ranging from 0.1 mg/kg to 20 mg/kg per day, more preferably at doses ranging from 1 to 20 mg/kg/day and most preferably at doses ranging from 2 to 10 mg/kg/day. The treatment may continue by continuous infusion or intermittent injection or infusion, at the same, reduced or increased dose per day for, e.g., 1 to 3 days, and additionally as determined by the treating physician. When administered intravenously, BPI protein products are preferably administered by an initial brief infusion followed by a continuous infusion. The preferred intravenous regimen is a 1 to 20 mg/kg brief intravenous infusion of BPI protein product followed by a continuous intravenous infusion at a dose of 1 to 20 mg/kg/day, continuing for up to one week. A particularly preferred intravenous dosing regimen is a 1 to 4 mg/kg initial brief intravenous infusion followed by a continuous intravenous infusion at a dose of 1 to 4 mg/kg/day, continuing for up to 72 hours.

Topical routes include administration in the form of salves, creams, jellies, ophthalmic drops or ointments (as described in co-owned, co-pending U.S. application Ser. No. 08/557,289 filed Nov. 14, 1995 and U.S. Pat. No. 5,686,414 and corresponding International Publication Nos. WO 97/17990 (PCT/US96/18632) and WO 97/17989 (PCT/US96/18416), all of which are incorporated herein by reference), ear drops, suppositories, irrigation fluids (for, e.g., irrigation of wounds) or medicated shampoos. For example, for topical administration in drop form, about 10 to 200 μL of a BPI protein product composition may be applied one or more times per day as determined by the treating physician.

Those skilled in the art can readily optimize effective dosages and administration regimens for therapeutic compositions comprising BPI protein product, as determined by good medical practice and the clinical condition of the individual patient.

Other aspects and advantages of the present invention will be understood upon consideration of the following illustrative examples. Example 1 addresses the construction of an expression vector, pING1742, encoding rBPI(10–193) C132A. Example 2 addresses transformation of CHO cells with pING1742 and selection of the highest producing clones secreting rBPI(10–193)C132A. Example 3 addresses the production and purification of rBPI(10–193)C132A in 2-L and 500-L fermenters. Example 4 addresses the biochemical characterization of rBPI(10–193)C132A and $rBPI_{21}$. Examples 5, 6 and 7 respectively address the in vitro LPS-binding activity in a competition binding assay and in an assay measuring rate of complex formation using rate nephelometry, bactericidal activity, and LPS neutralization activity of rBPI(10–193)C132A as compared to $rBPI_{21}$. Example 8 addresses the in vivo activity of rBPI(10–193) C132A.

EXAMPLE 1

Construction of Expression Vector pING1742

The rBPI(10–193)C132A expression vector, pING1742, was constructed as follows. The expression vector pING4155 was first constructed by ligating a BamHI-BsaI fragment containing the neo gene from pING3174 with a BsaI-XhoI of fragment containing the CMV promoter and $rBPI_{21}$ gene from pING4144 (including an optimized Kozak translation initiation site at residue −27 of the signal) and an XhoI-BamHI fragment containing the mouse (kappa) light chain 3' untranslated region from pING4537 (pING3174, pING4144 and pING4537 are described in U.S. Pat. No. 5,420,019, incorporated by reference). The resulting pING4155 vector contains the gene encoding $rBPI_{21}$ fused to the human IgG enhancer, the human CMV promoter, a 27 amino acid BPI leader sequence (amino acid residues −27 through −1 of SEQ ID NO: 2) and the mouse (kappa) light chain 3' untranslated region. It also contains the neo gene encoding neomycin phosphotransferase, for selection of transfectants resistant to the antibiotic Geneticin® (G418).

The vector pING1732 was produced by deleting the 0.7 kbp HindIII—HindIII fragment of pING4155 containing the human Ig enhancer. Then, the 27 nucleotides encoding amino acids 1 through 9 of the mature portion of $rBPI_{21}$ were deleted from pING1732 by overlap PCR mutagenesis using the following primers:

Primer 1: 5'-CTGCTCTAAAAGCTGCTGCAG-3' (SEQ ID NO: 3)

Primer 2: 5'-CCAGGCCCTTCTGGGAGGCCGCTGTCACGGCGG-3' (SEQ ID NO: 4)

Primer 3: 5'-GCCGTGACAGCGGCCTCCCAGAAGGGCCTGGAC-3' (SEQ ID NO: 5)

Primer 4: 5'-CTGGGAACTGGGAAGCTG-3' (SEQ ID NO: 6)

Overlapping complementary primers 2 and 3 incorporated the 27 bp deletion of nucleotides encoding amino acids 1 through 9, while primers 1 and 4 encoded nucleotides immediately upstream and downstream, respectively, of unique SalI and EcoRI sites in pING1732. First, fragments were obtained by PCR amplification using the combination of oligonucleotide primers 1 and 3, and primers 2 and 4. After these individual fragments were obtained, they were annealed, extended and re-amplified using primers 1 and 4. This amplified fragment was then digested with SalI and EcoRI and cloned into SalI-EcoRI-digested pING1732 to generate the plasmid pING1742.

To confirm that no mutations had occurred during PCR, the SalI-EcoRI region from pING1742 was sequenced. No changes were observed in the mature coding region for BPI. However, a two base-pair change (ACC->GCT) was found in DNA encoding the signal sequence, which resulted in the conversion of a Thr to an Ala at amino acid position −6 relative to the start of the mature protein sequence.

EXAMPLE 2

Transformation of CHO Cells with pING1742

CHO-K1 cells (American Type Culture Collection (ATCC) Accession No. CCL61) were adapted to growth in serum-free Ex-Cell 301 medium as follows. CHO-K1 cells grown in Ham's F12 medium were trypsinized, centrifuged and resuspended in Ex-Cell 301 medium. Cells were grown in a 125-ml flask at 100 rpm and passaged every two to three days in either a 125-ml or 250-ml flask.

These Ex-Cell 301-adapted CHO cells were transfected by electroporation with pING1742. Prior to transfection, pING1742 was digested with NotI, which linearizes the plasmid. Following a 48-hour recovery, cells were plated at approximately $10^4$ cells/well into 96-well plates containing Ex-Cell 301 medium supplemented with 0.6 mg/mL G418 (Life Technologies, Gaithersburg, Md.). At approximately 2 weeks, supernatants from approximately 250 wells containing single colonies were screened by EUTSA for the presence of BPI-reactive protein using an anti-BPI monoclonal antibody.

Fifteen clones having the highest expression levels were transferred to 24-well plates containing Ex-Cell 301 medium. To screen for productivity, the cells were grown in 24-well plates containing Ex-Cell medium supplemented with 2 % FBS and 40 µL sterile S-Sepharose beads for 10 days, after which the beads were removed, washed with low salt buffer (0.1 M NaCl in 10 mM Na acetate, pH 4.0) and the BPI eluted with 1.5 M NaCl in the same buffer. The levels of secreted rBPI(10–193)C132A were determined by ELISA. Western blot analysis of eluates run on a 12 % non-reducing SDS gel revealed a prominent band which migrated slightly faster than $rBPI_{21}$.

The top eight producers were transferred to sterile 125 mL Erlenmeyer flasks and grown in Ex-Cell medium. These cells were evaluated again for productivity by growing them in flasks containing Ex-Cell 301 medium supplemented with 2% FBS and 1 % (V/V) sterile S-sepharose beads. The rBPI(10–193)C132A was eluted from the S-Sepharose beads that had been incorporated in the culture medium and the levels of rBPI(10–193)C132A determined by HPLC. Clone 139, which was among the highest producers, was chosen for further growth and product production.

EXAMPLE 3

Production and Purification of rBPI(10–193)C132A

Large quantities of rBPI(10–193)C132A were produced for characterization by growing Clone 139 cells in 2-liter research fermenters (Biolafitte, St. Germain en Laye, France) and then in a 500 liter ABEC fermenter (ABEC, Allentown, Pa.). Protein product obtained from the 2-liter fermenters was used for the in vitro studies described below, while product obtained from the 500 liter fermenter was used for animal toxicology and efficacy studies.

A. Growth in Two-Liter Fermenters

Clone 139 cells were passaged in spinner flasks of increasing volumes containing Ex-Cell medium supplemented with 1% FBS until sufficient volume and cell density was achieved to inoculate the 2 liter bioreactors at approximately $2\times10^5$ cells/mL. Cells were grown in three 2-liter fermenters in Ex-Cell medium supplemented with 1% FBS, at 37 ° C., pH 7.2, 150 rpm with dissolved oxygen maintained at 5–10%. Large sterile SP-Sepharose beads (Pharmacia and Upjohn, Piscataway, N.J.) were added at 1.5% (V/V). The initial glucose level was approximately 3.5 g/L and glucose was pulsed daily to 3 g/L during the course of the run. The fermentation was terminated at 238 hours, at which time the cell viabilities were from 63%, 80% and 84%.

Following fermentation, the beads from each fermenter were harvested, allowed to settle, and washed several times with 10 mM Na phosphate/0.15M NaCl, pH 7.0, to remove cellular components and weakly bound impurities from the beads. The washed beads were packed into a column, washed with 10 mM Na phosphate, 0.25 M NaCl, pH 7.0, and eluted with the same buffer containing 0.8 M NaCl, 5 mM glycine. The eluate was then diluted with three volumes of sterile water for injection (WFI), loaded onto a CM-spherodex column (Sepracor, Marlborough, Mass.) and washed with 10 mM Na phosphate, 0.25 M NaCl, pH 7.0, followed by 20 mM Na acetate, 0.2 M NaCl, pH 4.0, followed by 20 mM Na acetate, 0.3 M NaCl, pH 4.0, and sample was eluted at 1.0 M NaCl in the same buffer. Following concentration on a Centricon membrane with a 10,000 MW cutoff (Amicon, Beverly, Mass.), the eluate from the CM column was loaded onto a Sephacryl S-100 column (Pharmacia and Upjohn) equilibrated with 5 mM Na citrate, 0.15 M NaCl, pH 5.0. Fractions containing rBPI (10–193)C132A identified by absorbance at 280 nm were pooled, concentrated on an Amicon filter to 1.9 mg/mL and formulated with 0.002% polysorbate 80 (T Baker, Phillipsburg, N.J.), 0.2% poloxamer 188 (Pluronic F-68, BASF, Parsippany, N.J.). The final preparation was filter sterilized using a 0.2 µm filter.

B. Growth in 500-Liter Fermenter

Clone 139 cells were passaged in fetuin-free Ex-Cell medium with 1% FBS in a series of spinner flasks of increasing volumes to provide inoculum for the 35L Bellco spinner flask (Bellco Glass, Vineland, N.J.), which in turn provided the inoculum for the 500 liter ABEC fermenter. Cells were grown in complete Ex-Cell medium without fetuin but supplemented with 1% FBS, additional glucose (to 10 g/L) and glutamine (to 10 mM). The fermenter was operated in a fed-batch mode with one 0.5% Primatone RL supplement pulse and one glucose/glutamine pulse added during the run. Five to six liters of large SP-Sepharose beads were added 24 hours after the 500 liter fermenter was inoculated. The pH was controlled manually with 10% sodium bicarbonate to pH 7.0, oxygen was controlled at 5% and temperature at 37° C. Agitation was maintained at 25 rpm with two three-blade paddle impellers. The fermentation run was terminated at 184 hours, at which time the cell viability was 90%.

As described above for the 2-liter fermentation, the beads were allowed to settle following fermentation and then washed several times with low salt (0.1M) phosphate buffer. The steps for this purification were similar to those described above for the 2-liter samples except that a pH 3.0 viral inactivation step was included after elution from the S-Sepharose beads and a second CM-spherodex column was included as a concentration step. For the second CM column, the eluate was diluted with three volumes of WFI, the pH adjusted to 5.0, the column was equilibrated and washed with 20 mM Na acetate, 0.3 M NaCl, pH 5.0 and the sample was eluted at 1.0 M NaCl in the same buffer. The rBPI(10–193)C132A was eluted from the Sephacryl S-100 column in 5 mM Na citrate, 0.15 M NaCl, pH 5.0, adjusted to 2 mg/mL, and filtered through a 0.2 $\mu$m filter. The rBPI(10–193)C132A was then formulated with 0.002% polysorbate 80, 0.2% poloxamer 188, sterile filtered, and filled into 10 mL Type I glass serum vials.

EXAMPLE 4

Biochemical Characterization of rBPI(10–193) C132A

A. Protein from the 2-Liter Fermentations

The purified rBPI(10–193)C132A product from Example 3 was observed to be a single band that migrated slightly faster on SDS polyacrylamide gel electrophoresis (SDS-PAGO) than the rBPI$_{21}$ band, consistent with the deletion of nine N-terminal amino acids from rBPI$_{21}$. Sequence analysis demonstrated that the rBPI(10–193)C132A contained the predicted N-terminal sequence of SQKGLDYASQQG-TAALQKEL. On mass spectroscopy analysis (ESI-MS) two components were observed, one with a mass of 20,470 daltons, which was consistent with the predicted mass of 20,472 daltons for rBPI(10–193)C132A, and a second with a mass of 20,255 daltons, consistent with the predicted mass of 20,258 daltons for rBPI(10–191). The ion-exchange HPLC profiles (Hewlett-Packard, Model 1050, Palo Alto, Calif.) of rBPI(10–193)C132A and rBPI$_{21}$ both exhibited single peaks with similar retention times.

B. Protein from the 500-Liter Fermentation

On SDS-PAGE, the rBPI(10–193)C132A was a single band that migrated slightly faster than the rBPI$_{21}$ band. On mass spectroscopy, there was a major component with a mass of 20,471 daltons, which is consistent with the predicted mass of 20,474 Da for rBPI(10–193)C132A), and two minor components with a mass of 20,668 daltons, which is consistent with addition of N-Acetylhexosamine (predicted mass 20,677 daltons) and a mass of 20,843 daltons, which is consistent with addition of N-Acetylhexosamine plus hexose (predicted mass 20,839 daltons). A similar component with added N-Acetylhexosamine is routinely observed during production of rBPI$_{21}$.

On reverse phase HPLC (Shimadzu, Kyoto, Japan) both the rBPI(10–193)C132A and rBPI$_{21}$ eluted as one major peak and one minor peak. However, the rBPI(10–193) C132A peaks eluted slightly earlier than the corresponding rBPI$_{21}$ peaks in the control. The minor peak in the rBPI (10–193)C132A profile most likely represents the glycosylated forms identified in the mass spectrum. The ion-exchange HPLC profiles of rBPI(10–193)C132A and rBPI$_{21}$ both exhibited single peaks with similar retention times.

Tryptic mapping analysis was performed according to conventional methods. Acetone precipitated rBPI$_{21}$ or rBPI (10–193)C132A was first treated with dithiothreitol (DTT) followed by iodoacetamide and then with trypsin. The trypsin-treated product was analyzed by HPLC (Beckman Model 126) with a C18 column (Beckman Ultrasphere). In rBPI$_{21}$, there are two N-terminal tryptic fragments (T1 and Ala-T1) which result from imprecise cleavage of the leader sequence. As predicted, the tryptic map of the rBPI(10–193) C132A was similar to rBPI$_{21}$ except that the N-terminal fragments were missing.

EXAMPLE 5

In Vitro LPS-Binding Activity of rBPI(10–193) C132A

A. In a Competition Binding Assay

The ability of purified rBPI(10–193)C132A produced according to Example 3A and rBPI$_{21}$ to compete with labeled rBPI$_{21}$ for binding to LPS was evaluated in a competition binding assay. Briefly, a fixed concentration (0.5 nM) of $^{125}$-labeled rBPI$_{21}$ was mixed with unlabeled rBPI$_{21}$ or rBPI(10–193)C132A at dilutions ranging from 5 $\mu$M to 0.01 nM in DMEM containing HEPES buffer and bovine serum albumin (BSA) [U.S. Biochemicals, Cleveland, Ohio] and 100 $\mu$L of the mixture was added to Immulon-II plate wells pre-coated with 2.5 $\mu$g/mL E. coli J5 LPS (Calbiochem, San Diego, Calif.). The plates were incubated at 4° C. for 5 hours and washed 3 times with the DMEM medium. 75 $\mu$L of 0.1 N NaOH was added and the bound $^{125}$I-rBPI$_{21}$ was removed and counted. The results demonstrated that both proteins competed similarly with radiolabeled rBPI$_{21}$.

B. In an Assay Measuring Rate of Complex Formation

The LPS binding activity of rBPI(10–193)C132A was compared to rBPI$_{21}$ using rate nephelometry. This approach for evaluating rBPI$_{21}$ binding to LPS measures the rate of increase of light scattering as a result of LPS-BPI protein product complex formation in solution. All of the experiments were performed with a Beckman Array 360 Rate Nephelometer which automatically mixes samples, measures light scattering and performs rate calculations.

Prior experiments using this approach examined optimal LPS species and concentration, assay specificity, assay reproducibility and correlation of assay results to bactericidal assays. It was observed that E. coli J5 LPS and lipid A formed complexes with rBPI$_{21}$ that could be measured in the nephelometer, but E. coli O111:B4 LPS did not form measurable complexes. Based on results of these studies, E. coli J5 LPS was chosen for use at a concentration (in the flow cell) of 49.4 to 61.7 $\mu$g/ml, depending on the LPS lot, in combination with rBPI$_{21}$ concentrations (in the flow cell) from 5 to 30 $\mu$g/ml. The optimal rBPI$_{21}$ concentration range, which must be determined for each LPS lot, was from about 15 to 25 $\mu$g/ml which represented the most linear portion of the curve. The optimal range for the aggregation rate RT) values was from 700 to 2000. Lower concentrations of rBPI$_{21}$ were needed to achieve the same aggregation rate values when the formulation buffer was changed to include PLURONIC P103 or when the NaCl concentration was increased. The addition of either recombinant lipopolysaccharide binding protein (rLBP$_{50}$) which binds to LPS, or heparin which binds to BPI protein products, inhibited the formation of rBPI$_{21}$-LPS aggregates, demonstrating the specificity of the interaction. Assay reproducibility was confirmed by testing multiple lots of BPI and testing the same lot of rBPI$_{21}$ multiple times. Nephelometric analysis of rBPI$_{21}$ samples that had been partially inactivated by treatment at 45° C. for one week correlated well with those from broth microdilution bactericidal assays with E. coli J5 cells.

Nephelometry experiments comparing rBPI(10–193) C132A and rBPI$_{21}$ were carried out as follows. Sonicated LPS [E. coli J5 LPS Lot No. 30119B from List Biochemicals] and either rBPI(10–193)C132A or rBPI$_{21}$ [both of which were formulated in 0.2% PLURONIC F68 (poloxamer 188), 0.002% TWEEN 80 (polysorbate 80), 5 mM citrate, pH 5.0, 150 mM NaCl] were diluted directly into a PBS buffer (supplemented with PEG) supplied by Beckman. The LPS concentration was fixed while the BPI protein product concentration varied within each experiment. Two concentrations of LPS were tested: 24.7 and 49.4 μg/ml LPS. Each reaction was initiated by addition of 600 μl of the PBS-PEG buffer to the flow cell followed by 42 μl of the BPI protein product dilution. After a baseline was established, 42 μl of the E. coli J5 LPS solution was added. After addition of the last component, the nephelometer measures the rate of complex formation based on the extent of light scatter. The data were analyzed by dividing the RT values for each test sample containing a given BPI protein product concentrations by the corresponding RT values for the standard to generate a percent of control value. For each BPI protein product concentration tested, the maximum aggregation rate was determined and a curve generated. Only points to the left of the maximum value (point of equivalence) were used for comparative analysis of various BPI protein product samples. The relative activity of samples can be measured by comparing the RT values for test and standard lots in the linear region of the curves. Either a point to point or curve fit approach can be used.

In addition to testing purified rBPI(10–193)C132A and purified rBPI$_{21}$ [which contains about 7.8% rBPI(10–193) C132A], an equal mixture of these proteins as well as a rBPI$_{21}$ preparation with 16% rBPI(10–193)C132A was evaluated (at 49.4 μg/ml LPS only). The results demonstrated that at 49.4 μg/ml LPS, rBPI(10–193)C132A achieved aggregation rates similar to that of rBPI$_{21}$ at an approximately 25% lower concentration. The rBPI(10–193) C132A also achieved a higher maximum aggregation rate than that of rBPI$_{21}$ at both 24.7 and 49.4 μg/ml LPS. An equal mix of the two molecules yielded a curve that ran between rBPI$_{21}$ and rBPI(10–193) while the rBPI$_{21}$ lots with 7.8% and 16% 10–193 behaved in an identical manner to each other. A point to point analysis of the results (LPS at 49.4 μg/ml) revealed that the rBPI(10–193) was approximately twice as potent as rBPI$_{21}$ in this assay.

EXAMPLE 6

In Vitro Bactericidal Activity of rBPI(10–193) C132A

All of the assays in this example were conducted with rBPI(10–193)C132A produced in the 2-liter fermenters according to Example 3A.
A. Effect on E. coli in a Radial Diffusion Assay This radial diffusion assay compared the bactericidal effect of purified rBPI(10–193)C132A and rBPI$_{21}$ on E. coli J5, which is a UDP-galactose-4-epimerase "rough" mutant of the smooth strain E. coli 011B4, and is relatively sensitive to rBPI$_{21}$. E. coli J5 cells (Mannion et al., J. Clin. Invest., 85:853–860 (1990); List Biological Laboratories, Campbell, Calif.) were grown to exponential phase, centrifuged and washed twice in 10 mM Na phosphate, pH 7.4, and added at a final concentration of approximately $1 \times 10^6$ CFU/ml to molten agarose supplemented with 3% Trypticase Soy Broth (TSB, DIFCO Laboratories, Detroit, Mich.), 10 mM Na phosphate. Wells of 3 mm diameter were prepared in the hardened agarose and 5 μL of serially diluted rBPI$_{21}$ or rBPI(10–193)C132A was added to the wells. The plates were incubated at 37° C. for 3 hours to allow diffusion to occur, and then a molten agarose overlay containing 6% TSB was added. The plates were incubated overnight at 37° C. and the net area of inhibition was plotted vs. concentration. The results demonstrated that rBPI(10–193)C132A and rBPI$_{21}$ behaved in a similar manner in this assay.

B. Effect on S. Aureus L-Form in a Radial Diffusion Assay

This radial diffusion assay compared the bactericidal effect of purified rBPI(10–193)C132A and rBPI$_{21}$ on the gram-positive bacteria S. aureus grown as L-forms without their cell walls. As described in U.S. Pat. No. 5,578,572, incorporated herein by reference, S. aureus L-form cells were grown to log phase in heart infusion (HI) broth supplemented with 3.5% NaCl, 10 mM CaCl$_2$ and 1000 U/mL penicillin G. The cells were diluted to approximately either $5 \times 10^4$ or $5 \times 10^5$ cells/mL in molten 0.8% agarose containing the NaCl-supplemented HI medium, and 8 ml of the cell-agarose suspension was poured into 10 cm plates. Wells of 3 mm diameter were prepared, and 5 μL of serially diluted rBPI$_{21}$ or rBPI(10–193)C132A was added to the wells. The plates were incubated at 37° C for 24 hours and the net area of inhibition was plotted vs. concentration. The results demonstrated that both rBPI$_{21}$ and rBPI(10–193) C132A inhibited growth of the S. aureus L-forms, at cell densities of about $5 \times 10^4$ and $5 \times 10^5$, in a similar fashion in this assay.

C. Effect on E. coli J5 in a Broth Microdilution Assay

This broth microdilution assay compared the bactericidal effect of purified rBPI(10–193)C132A and rBPI$_{21}$ on E. coli J5. E. coli J5 cells were grown overnight in tryptone yeast extract (TYE) broth and then to logarithmic phase in TEA medium as previously described in Horwitz et al., Infect. Immun., 63:522–527 (1995). The cells were inoculated at approximately $1 \times 10^4$ and $1 \times 10^5$ cells/ML in heart infusion (HI) broth, and 95 μL was added to 96 well plates. Five μL of various dilutions of rBPI(10–193)C132A or rBPI$_{21}$, prepared in formulation buffer, was added to each well and the plates were incubated at 37° C. for 24 hours. The results demonstrated that rBPI(10–193)C132A and rBPI$_{21}$ have similar activities in these assays.

EXAMPLE 7

In Vitro LPS Neutralization Activity of rBPI (10–193)C132A

The assay in section A of this example was conducted with rBPI(10–193)C132A produced in the 2-liter fermenters according to Example 3A, while the assay in section B of this example was conducted with rBPI(10–193)C132A produced in the 500-liter fermenter according to Example 3B.
A. Activity in a RAW Cell Proliferation Assay The RAW cell proliferation assay was used to compare the in vitro LPS neutralization activity of rBPI$_{21}$ and rBPI (10–193)C132A. In this assay, the LPS inhibits the proliferation of RAW cells, and rBPI$_{21}$ neutralizes this effect of LPS.

Mouse RAW 264.7 cells (ATCC Accession No. T1B71), maintained in RPMI 1640 medium (GIBCO), supplemented with 10 mM HEPES buffer (pH 7.4), 2 mM L-glutamine, penicillin (100 U/mL), streptomycin (100 μg/mL), 0.075% sodium bicarbonate, 0.15M 2-mercaptoethanol and 10% fetal bovine serum (Hyclone, Inc., Logan, Utah), were first induced by incubation in the presence of 50 U/mL recombinant mouse γ-interferon (Genzyme, Cambridge, Mass.) for 24 hours prior to assay. Induced cells were then mechanically collected and centrifuged at 500×g at 4° C. and then resuspended in 50 mL RPMI 1640 medium (without supplements), re-centrifuged and again resuspended in RPMI 1640 medium (without supplements). The cells were counted, their concentration adjusted to 2×10$^5$ cells/mL and 100 μL aliquots were added to each well of a 96-well plate.

The cells were then incubated for about 15 hours with $E.$ $coli$ O113 LPS (Control Standard, Assoc. of Cape Code, Woods Hole, Mass.), which was added in 100 μL/well aliquots at a concentration of 1 ng/mL in serum-free RPMI 1640 medium (this concentration being the result of titration experiments in which LPS concentration was varied between 50 pg/mL and 100 ng/mL). This incubation was performed in the absence or presence of rBPI$_{21}$ or rBPI (10–193)C132A in varying concentrations between 25 ng/mL and 50 μg/mL. Recombinant human rBPI$_{21}$, also designated rBPI$_{21}$Δcys, which is rBPI 1–193 with alanine substituted at position 132 for cysteine [see co-owned U.S. Pat. No. 5,420,019], was used as a positive control at a concentration of 1 μg/mL. Cell proliferation was quantitatively measured by the addition of 1 μCi/well [$^3$]-thymidine 5 hours after the time of initiation of the assay. After the 15-hour incubation, labeled cells were harvested onto glass fiber filters with a cell harvester (Inotech Biosystems, INB-384, Sample Processing and Filter Counting System, Lansing, Mich.). The LPS-mediated inhibition of RAW 264.7 cell proliferation is dependent on the presence of LBP, as added to the reaction mixture either as a component of serum or as recombinant LBP (at a concentration of 1 μg/mL.

In these experiments, both rBPI$_{21}$ and rBPI(10–193) C132A similarly inhibited the LPS-mediated inhibition of RAW cell proliferation.

B. Activity in a TNF Inhibition Assay

A tumor necrosis factor (TNF) inhibition assay was used to compare the in vitro LPS neutralization activity of rBPI$_{21}$ and the rBPI(10–193)C132A. In this assay, the LPS, in combination with purified LBP (or serum containing LBP) stimulates synthesis of TNF by THP-1 cells (a human monocyte cell line), and rBPI$_{21}$ neutralizes this effect of LPS.

THP.1 cells (ATCC Accession No. TIB-202) were maintained in RPMI (GibcoBRL, Gaithersburg, Md.) with 10% FBS and were cultured in RPMI with 10% FBS plus 50 ng/ml 1,25 dihydroxy vitamin D (BIOMOL Research Laboratories Inc. Plymouth Meeting, Pa.) for three days prior to treatment with LPS to induce CD14 expression. Before inducing with LPS, cells were washed three times with RPMI and suspended in either RPMI with 10% FBS or in serum free medium [RPMI supplemented with 1% HB101 (Irvine Scientific, Santa Ana, Calif.)]. Expression of TNF was induced with 1 ng/ml $E.$ $coli$ 0128 LPS (Sigma, St. Louis, Mo.) in 96 well plates with approximately 5×10$^4$ cells per well. Plates were incubated for three hours at 37° C., 5% CO$_2$, then an aliquot of the supernatant liquid was removed and assayed for TNF by the WEHI 164 toxicity assay, using CellTiter 96™ AQ (Promega Corp., Madison, Wis.) to monitor cell viability. Recombinant human TNFα (Genzyme Diagnostics, Cambridge, Mass.) was used as a positive standard. Both rBPI$_{21}$ and rBPI(10–193)C132A similarly inhibited LPS-induced stimulation of TNF synthesis.

EXAMPLE 8

In Vivo Biological Activity of rBPI(10–193)C132A

The in vivo assays described below were performed using the purified rBPI(10–193)C132A produced in the 500-liter fermenter according to Example 3B.

A. Toxicity Study in Rats

Toxicity profiles of rBPI$_{21}$ and rBPI(10–193)C132A were compared in rats. In this study, groups of six male and six female Sprague-Dawley rats received either vehicle control (formulation buffer), low (50 mg/kg/day) or high (120 mg/kg/day) doses of either rBPI$_{21}$ or rBPI(10–193)C132A. Doses were administered by continuous intravenous infusion via an indwelling femoral catheter for three consecutive days at an infusion rate of 4.2 mL/kg/hour (100 mL/kg/day). Clinical observations were recorded at least twice daily and body weights were recorded daily. Blood and urine samples were collected near termination for hematology, clinical chemistry and urinalysis assessments. At termination, organs were weighed and tissues collected by histopathological examination. There were no deaths or significant test article-related effects. The data indicated similar toxicity profiles for rBPI$_{21}$ and the rBPI(10–193)C132A when given by continuous infusion.

B. Pharmacokinetics

The pharmacokinetics of rBPI$_{21}$ and rBPI(10–193)C132A at 2 mg/kg were investigated in rats. The plasma clearances of rBPI$_{21}$ and rBPI(10–193)C132A were well described by a tri-exponential pharmacokinetic disposition function. No statistical differences in the pharmacokinetic parameters among the rBPI products were determined (non parametric Wicoxon rank test, p<0.05). Most of the administered drug (>96%) was cleared with an alpha phase half-life of 0.2–0.4 minutes and a beta half-life of 3.9–4.3 minutes, while the remainder was cleared during the gamma phase with a half-life of 27–33 minutes. The volume of distribution of the central compartment (Vc) was 41–45 mL/kg, and the clearance rate (CL) was 24–30 mL/min/kg. The steady state volume of distribution was 152–184 mL/kg.

C. Efficacy in Mouse Endotoxin Challenge

Two separate studies were conducted to examine relative potencies of rBPI$_{21}$ and rBPI(10–193)C132A in a mouse model of lethal endotoxemia generally according to Ammons et al., in "Novel Therapeutic Strategies in the Treatment of Sepsis," Morrison and Ryan, eds., Marcel Dekker, New York (1996), pages 55–69. In both studies, there were 14 mice in each treatment and control group. In the first study, CD1 mice were challenged intravenously with 25 mg/kg of lipopolysaccharide (LPS) from $E.$ $coli$ O111:B4. Immediately after the challenge, the mice were treated intravenously with rBPI$_{21}$ or rBPI(10–193)C132A at doses of 15, 20, 25 and 30 mg/kg, or with the control vehicle (formulation buffer only). Mortality was recorded twice daily for seven days.

The results from the first study, shown in Table 1 below, indicate that treatment with both rBPI(10–193)C132A and rBPI$_{21}$ significantly increased survival compared to the vehicle controls. In addition, rBPI(10–193)C132A was at least two-fold more potent than rBPI$_{21}$ with a similar survival benefit seen with a two-fold lower dose of rBPI (10–193)C132A compared to rBPI$_{21}$.

TABLE 1

| | No. of Survivors out of 15 | | |
|---|---|---|---|
| Dose (mg/kg) | Control | rBPI$_{21}$ | rBPI(10–193)C132A |
| 0(Vehicle) | 0 | NA[1] | NA |
| 15 | | 0 | 15**,## |
| 20 | | 4 | 15**,# |
| 25 | | 11** | 15** |
| 30 | | 13** | 13** |

[1]NA, Not Applicable
**, $p < 0.01$ vs. control
, $p < 0.05$ vs. rBPI$_{21}$
, $p < 0.01$ vs. control In the second study, a wider range of rBPI(10–193)C132A doses (5, 10, 15, 20, 25, 30 mg/kg) was studied. The results, shown in Table 2 below, confirm that while both rBPI$_{21}$ and rBPI(10–193)C132A offered a significant survival benefit over the control, as in the first study, rBPI(10–193)C132A was at least two-fold more potent, achieving similar efficacy as rBPI$_{21}$ with a 2-fold lower dose.

TABLE 2

| | No. of Survivors out of 15 | | |
|---|---|---|---|
| Dose (mg/kg) | Control | rBPI$_{21}$ | rBPI(10–193)C132A |
| 0(Vehicle) | 2 | NA[1] | NA |
| 5 | | ND[1] | 3 |
| 10 | | ND | 10* |
| 15 | | ND | 14** |
| 20 | | 7 | 14**,# |
| 25 | | 13** | 15** |
| 30 | | 14** | 15* |

[1]NA, Not Applicable; ND, Not Done
**, $p < 0.05$ vs. control
**, $p < 0.01$ vs. control
, $p < 0.05$ vs. rBPI$_{21}$

D. Efficacy In Murine Model Of Lethal Bacteremia

Two separate studies were conducted to examine the relative potencies or rBPI$_{21}$ and rBPI(10–193)C132A in a mouse model of lethal bacteremia. In both studies, there were 20 mice per treatment group. In the first study, CD1 mice were challenged with $6.8 \times 10^7$ colony forming units (CFU) of *E. coli* O7:K1 administered intravenously. Immediately after the challenge, the mice were treated intravenously with rBPI$_{21}$ or rBPI(10–193)C132A at doses of 10, 20 and 30 mg/kg, or with control vehicle (formulation buffer only). Mortality was recorded twice daily for seven days.

The results from the first study, shown in Table 3 below, demonstrate a significant increase in survival for the groups treated with 10 and 30 mg/kg of rBPI$_{21}$ ($p<0.05$ vs. control). While a similar significant increase in survival was not observed with the rBPI(10–193)C132A vs. control, there was not a significant difference in survival advantage between the rBPI$_{21}$ and rBPI(10–193)C132A -treated groups in this study.

TABLE 3

| | No. of Survivors out of 20 | | |
|---|---|---|---|
| Dose (mg/kg) | Control | rBPI$_{21}$ | rBPI(10–193)C132A |
| 0(Vehicle) | 6 | | NA |
| 10 | | 14* | 12 |

TABLE 3-continued

| | No. of Survivors out of 20 | | |
|---|---|---|---|
| Dose (mg/kg) | Control | rBPI$_{21}$ | rBPI(10–193)C132A |
| 20 | | 12 | 10 |
| 30 | | 14* | 10 |

*, $p < 0.05$ vs. control

To more fully characterize the effects of rBPI$_{21}$ and rBPI(10–193)C132A in this model, a second study was conducted in which a wider range of doses was studied. In this study, CD1 mice were challenged with $2.57 \times 10^8$ colony forming units (CFU) of *E. coli* O7:K1 administered intravenously. Immediately after the challenge, the mice were treated intravenously with 1.0, 3.0, 10 and 30 mg/kg rBPI$_{21}$ and 0.3, 1.0, 3.0, 10 and 30 mg/kg rBPI(10–193)C132A. The results, shown in Table 4 below, indicate that both proteins provided protection, and that there was no significant difference in the protective effects of the two variants at any dose.

TABLE 4

| | No. of Survivors out of 20 | | |
|---|---|---|---|
| Dose (mg/kg) | Control | rBPI$_{21}$ | rBPI(10–193)C132A |
| 0(Vehicle) | 6 | | |
| 0.3 | | ND[1] | 6 |
| 1.0 | | 4 | 6 |
| 3.0 | | 9 | 10* |
| 10 | | 13** | 8 |
| 30 | | 11* | 14** |

[1]ND, Not Done
*, $p < 0.05$ vs. control
**, $p < 0.01$ vs. control

E. Cardiovascular Effects in Conscious Rats

A series of experiments were conducted to determine the relative effects of rBPI$_{21}$ and rBPI(10–193)C132A on blood pressure in rats. Each rat was anesthetized with a mixture of ketamine (Fort Dodge Labs, Fort Dodge, Id.) and Rompum (Bayer Corp., Shawnee Mission, Kans.). A catheter was then placed in the right carotid artery and connected to a pressure transducer to record blood pressure. A second catheter was placed in the right jugular vein to inject rBPI or vehicle. The rats were then allowed to recover before the experiments began. Experiments were initiated when the rats were alert, mobile and when blood pressure was stable within the normal range. rBPI$_{21}$, rBPI(10–193)C132A or control vehicle (formulation buffer) were then injected as a bolus over 15 seconds and mean arterial blood pressure (mm Hg) was recorded over the next 60 minutes.

In preliminary experiments, it was determined that doses of 20 and 30 mg/kg of rBPI$_{21}$ had no significant effect on blood pressure relative to the vehicle but that a dose of 40 mg/kg resulted in a significant decrease in blood pressure that was evident within 5 minutes. This hypotensive response was greatest 15 minutes after the injection when blood pressure had decreased by 48±12 mm Hg (mean ±SE; $p>0.05$). After 60 minutes, the blood pressure of the rBPI$_{21}$-treated animals recovered and was not significantly different from that of the vehicle-treated animals.

To compare effects of rBPI$_{21}$ and rBPI(10–193)C132A, groups of 5 rats were given 40 mg/kg of each drug substance or vehicle control, and blood pressure responses were analyzed as area under the curve (AUC). FIG. 1 shows that, as previously observed, rBPI$_{21}$ caused a significant drop in blood pressure indicated by the elevated AUC relative to the vehicle control. By comparison, rBPI(10–193)C132A had no significant effect on blood pressure compared with the vehicle control. A dose of 50 mg/kg rBPI$_{21}$ (N=4 rats) had an even greater hypotensive effect than that of the 40 mg/kg dose as indicated by a further increase in the AUC in FIG. 1. At this higher dose, some reduction in blood pressure also occurred in rats administered rBPI(10–193)C132A (N=3), but this effect was not significant compared to the vehicle control.

Numerous modifications and variations of the above-described invention are expected to occur to those of skill in the art. Accordingly, only such limitations as appear in the appended claims should be placed thereon.

SEQUENCE LISTING

<160> NUMBER OF SEQ ID NOS: 6

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
<220> FEATURE:
<221> NAME/KEY: mat_peptide
<222> LOCATION: (124)..(1491)
<220> FEATURE:
<223> OTHER INFORMATION: rBPI

<400> SEQUENCE: 1

```
caggccttga ggttttggca gctctggagg atg aga gag aac atg gcc agg ggc      54
                                Met Arg Glu Asn Met Ala Arg Gly
                                -30                     -25 cct tgc aac gcg ccg aga tgg gtg tcc ctg atg gtg ctc gtc gcc ata     102
Pro Cys Asn Ala Pro Arg Trp Val Ser Leu Met Val Leu Val Ala Ile
            -20                 -15                 -10 ggc acc gcc gtg aca gcg gcc gtc aac cct ggc gtc gtg gtc agg atc     150
Gly Thr Ala Val Thr Ala Ala Val Asn Pro Gly Val Val Val Arg Ile
        -5                  -1   1                   5 tcc cag aag ggc ctg gac tac gcc agc cag cag ggg acg gcc gct ctg     198
Ser Gln Lys Gly Leu Asp Tyr Ala Ser Gln Gln Gly Thr Ala Ala Leu
 10                  15                  20                  25 cag aag gag ctg aag agg atc aag att cct gac tac tca gac agc ttt     246
Gln Lys Glu Leu Lys Arg Ile Lys Ile Pro Asp Tyr Ser Asp Ser Phe
                 30                  35                  40 aag atc aag cat ctt ggg aag ggg cat tat agc ttc tac agc atg gac     294
Lys Ile Lys His Leu Gly Lys Gly His Tyr Ser Phe Tyr Ser Met Asp
             45                  50                  55 atc cgt gaa ttc cag ctt ccc agt tcc cag ata agc atg gtg ccc aat     342
Ile Arg Glu Phe Gln Leu Pro Ser Ser Gln Ile Ser Met Val Pro Asn
         60                  65                  70 gtg ggc ctt aag ttc tcc atc agc aac gcc aat atc aag atc agc ggg     390
Val Gly Leu Lys Phe Ser Ile Ser Asn Ala Asn Ile Lys Ile Ser Gly
     75                  80                  85 aaa tgg aag gca caa aag aga ttc tta aaa atg agc ggc aat ttt gac     438
Lys Trp Lys Ala Gln Lys Arg Phe Leu Lys Met Ser Gly Asn Phe Asp
 90                  95                 100                 105 ctg agc ata gaa ggc atg tcc att tcg gct gat ctg aag ctg ggc agt     486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc     534
Asn Pro Thr Ser Gly Lys Pro Thr Ile Thr Cys Ser Ser Cys Ser Ser
            125                 130                 135 cac atc aac agt gtc cac gtg cac atc tca aag agc aaa gtc ggg tgg     582
His Ile Asn Ser Val His Val His Ile Ser Lys Ser Lys Val Gly Trp
        140                 145                 150 ctg atc caa ctc ttc cac aaa aaa att gag tct gcg ctt cga aac aag     630
```

-continued

```
Leu Ile Gln Leu Phe His Lys Lys Ile Glu Ser Ala Leu Arg Asn Lys
    155                 160                 165 atg aac agc cag gtc tgc gag aaa gtg acc aat tct gta tcc tcc aag        678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct        726
Leu Gln Pro Tyr Phe Gln Thr Leu Pro Val Met Thr Lys Ile Asp Ser
                190                 195                 200 gtg gct gga atc aac tat ggt ctg gtg gca cct cca gca acc acg gct        774
Val Ala Gly Ile Asn Tyr Gly Leu Val Ala Pro Pro Ala Thr Thr Ala
            205                 210                 215 gag acc ctg gat gta cag atg aag ggg gag ttt tac agt gag aac cac        822
Glu Thr Leu Asp Val Gln Met Lys Gly Glu Phe Tyr Ser Glu Asn His
        220                 225                 230 cac aat cca cct ccc ttt gct cca cca gtg atg gag ttt ccc gct gcc        870
His Asn Pro Pro Pro Phe Ala Pro Pro Val Met Glu Phe Pro Ala Ala
    235                 240                 245 cat gac cgc atg gta tac ctg ggc ctc tca gac tac ttc ttc aac aca        918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga        966
Ala Gly Leu Val Tyr Gln Glu Ala Gly Val Leu Lys Met Thr Leu Arg
                270                 275                 280 gat gac atg att cca aag gag tcc aaa ttt cga ctg aca acc aag ttc       1014
Asp Asp Met Ile Pro Lys Glu Ser Lys Phe Arg Leu Thr Thr Lys Phe
            285                 290                 295 ttt gga acc ttc cta cct gag gtg gcc aag aag ttt ccc aac atg aag       1062
Phe Gly Thr Phe Leu Pro Glu Val Ala Lys Lys Phe Pro Asn Met Lys
        300                 305                 310 ata cag atc cat gtc tca gcc tcc acc ccg cca cac ctg tct gtg cag       1110
Ile Gln Ile His Val Ser Ala Ser Thr Pro Pro His Leu Ser Val Gln
    315                 320                 325 ccc acc ggc ctt acc ttc tac cct gcc gtg gat gtc cag gcc ttt gcc       1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac       1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga       1254
Thr Thr Gly Ser Met Glu Val Ser Ala Glu Ser Asn Arg Leu Val Gly
            365                 370                 375 gag ctc aag ctg gat agg ctg ctc ctg gaa ctg aag cac tca aat att       1302
Glu Leu Lys Leu Asp Arg Leu Leu Leu Glu Leu Lys His Ser Asn Ile
        380                 385                 390 ggc ccc ttc ccg gtt gaa ttg ctg cag gat atc atg aac tac att gta       1350
Gly Pro Phe Pro Val Glu Leu Leu Gln Asp Ile Met Asn Tyr Ile Val
    395                 400                 405 ccc att ctt gtg ctg ccc agg gtt aac gag aaa cta cag aaa ggc ttc       1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag       1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa           1491
Pro His Gln Asn Phe Leu Leu Phe Gly Ala Asp Val Val Tyr Lys
            445                 450                 455 tgaaggcacc agggtgccg ggggctgtca gccgcacctg ttcctgatgg gctgtggggc      1551
accggctgcc tttccccagg gaatcctctc cagatcttaa ccaagagccc cttgcaaact    1611
```

-continued

```
tcttcgactc agattcagaa atgatctaaa cacgaggaaa cattattcat tggaaaagtg    1671
catggtgtgt attttaggga ttatgagctt ctttcaaggg ctaaggctgc agagatattt    1731
cctccaggaa tcgtgtttca attgtaacca agaaatttcc atttgtgctt catgaaaaaa    1791
aacttctggt ttttttcatg tg                                             1813
```

<210> SEQ ID NO 2
<211> LENGTH: 487
<212> TYPE: PRT
<213> ORGANISM: Homo sapiens

<400> SEQUENCE: 2

```
Met Arg Glu Asn Met Ala Arg Gly Pro Cys Asn Ala Pro Arg Trp Val
    -30             -25                 -20

Ser Leu Met Val Leu Val Ala Ile Gly Thr Ala Val Thr Ala Ala Val
-15             -10                  -5             -1   1

Asn Pro Gly Val Val Arg Ile Ser Gln Lys Gly Leu Asp Tyr Ala
             5                  10                 15

Ser Gln Gln Gly Thr Ala Ala Leu Gln Lys Glu Leu Lys Arg Ile Lys
        20                  25                 30

Ile Pro Asp Tyr Ser Asp Ser Phe Lys Ile Lys His Leu Gly Lys Gly
    35                  40                  45

His Tyr Ser Phe Tyr Ser Met Asp Ile Arg Glu Phe Gln Leu Pro Ser
50                  55                  60                  65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe
            85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305
```

```
Ala Lys Lys Phe Pro Asn Met Lys Ile Gln Ile His Val Ser Ala Ser
            310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
        355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
                405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
        435                 440                 445

Gly Ala Asp Val Val Tyr Lys
450                 455
```

\<210\> SEQ ID NO 3
\<211\> LENGTH: 21
\<212\> TYPE: DNA
\<213\> ORGANISM: Artificial Sequence
\<220\> FEATURE:
\<223\> OTHER INFORMATION: Description of Artificial Sequence: primer

\<400\> SEQUENCE: 3 ctgctctaaa agctgctgca g                                                 21

\<210\> SEQ ID NO 4
\<211\> LENGTH: 33
\<212\> TYPE: DNA
\<213\> ORGANISM: Artificial Sequence
\<220\> FEATURE:
\<223\> OTHER INFORMATION: Description of Artificial Sequence: primer

\<400\> SEQUENCE: 4 ccaggccctt ctgggaggcc gctgtcacgg cgg                                    33

\<210\> SEQ ID NO 5
\<211\> LENGTH: 33
\<212\> TYPE: DNA
\<213\> ORGANISM: Artificial Sequence
\<220\> FEATURE:
\<223\> OTHER INFORMATION: Description of Artificial Sequence: primer

\<400\> SEQUENCE: 5 gccgtgacag cggcctccca gaagggcctg gac                                    33

\<210\> SEQ ID NO 6
\<211\> LENGTH: 18
\<212\> TYPE: DNA
\<213\> ORGANISM: Artificial Sequence
\<220\> FEATURE:
\<223\> OTHER INFORMATION: Description of Artificial Sequence: primer

\<400\> SEQUENCE: 6 ctgggaactg ggaagctg                                                     18

What is claimed are:

1. An isolated polynucleotide encoding a bactericidal/permeability-increasing protein (BPI) deletion analog consisting of amino acid residues 10 through 193 of mature human BPI (SEQ ID NO:2), wherein a cysteine residue at position 132 is replaced by a different amino acid and wherein the amino acid at position number 185 is selected from the group consisting of lysine and glutamic acid.

2. The polynucleotide of claim 1 wherein said cysteine residue at position 132 is replaced by alanine.

3. The polynucleotide of claim 1 further comprising nucleotides encoding the twenty-seven amino acid leader sequence of BPI (amino acid residues −27 through −1 of SEQ ID NO: 2).

4. The polynucleotide of claim 1 which is a DNA.

5. An expression vector comprising the DNA according to claim 4.

6. A host cell stably transformed or transfected with the DNA of claim 4 in a manner allowing expression in said host cell of said polypeptide deletion analog.

7. A eukaryotic host cell according to claim 6.

8. The host cell of claim 7 which is a CHO cell.

9. A method for producing a BPI deletion analog polypeptide comprising growing a host cell according to claim 6 in a suitable culture medium and isolating said polypeptide from said host cell or said culture medium.

10. The polynucleotide of claim 1 wherein said cysteine residue at position 132 is replaced by a nonpolar amino acid selected from the group consisting of alanine and serine.

* * * * *